(12) United States Patent
O'Laughlin

(10) Patent No.: US 9,044,216 B2
(45) Date of Patent: Jun. 2, 2015

(54) BIOPSY NEEDLE ASSEMBLY

(75) Inventor: Michael O'Laughlin, St. Louis, MO (US)

(73) Assignee: Best Medical International, Inc., Springfield, VA (US)

( * ) Notice: Subject to any disclaimer, the term of this patent is extended or adjusted under 35 U.S.C. 154(b) by 1115 days.

(21) Appl. No.: 12/834,357

(22) Filed: Jul. 12, 2010

(65) Prior Publication Data
US 2012/0010511 A1 Jan. 12, 2012

(51) Int. Cl.
*A61B 17/32* (2006.01)
*A61B 10/00* (2006.01)
*A61B 8/12* (2006.01)
*A61B 10/02* (2006.01)

(52) U.S. Cl.
CPC ..... *A61B 10/0241* (2013.01); *A61B 2010/0208* (2013.01); *A61B 8/12* (2013.01)

(58) Field of Classification Search
USPC .......................... 600/562–568; 606/167, 170
See application file for complete search history.

(56) References Cited

U.S. PATENT DOCUMENTS

| | | | |
|---|---|---|---|
| 4,374,525 A | 2/1983 | Baba | |
| 4,702,261 A | 10/1987 | Cornell et al. | |
| 4,756,313 A | 7/1988 | Terwilliger | |
| 4,757,818 A | 7/1988 | Angelsen | |
| 4,802,458 A | 2/1989 | Finsterwald et al. | |
| 4,819,650 A | 4/1989 | Goldstein | |
| 4,841,979 A | 6/1989 | Dow et al. | |
| 4,917,096 A | 4/1990 | Englehart | |
| 4,944,308 A | 7/1990 | Akerfeldt | |
| 5,048,529 A | 9/1991 | Blumenthal | |
| 5,050,610 A | 9/1991 | Oaks et al. | |
| 5,054,491 A | 10/1991 | Saito et al. | |
| 5,070,879 A | 12/1991 | Herres | |
| 5,090,414 A | 2/1992 | Takano | |
| 5,105,819 A | 4/1992 | Wollschlager et al. | |
| 5,152,294 A | 10/1992 | Mochizuki et al. | |
| 5,159,931 A | 11/1992 | Pini | |

(Continued)

FOREIGN PATENT DOCUMENTS

| | | |
|---|---|---|
| EP | 0142862 | 5/1985 |
| EP | 0453014 | 10/1991 |

(Continued)

OTHER PUBLICATIONS

U.S. Appl. No. 60/493,406, filed Aug. 7, 2003, Fichtinger et al.

(Continued)

*Primary Examiner* — Max Hindenburg
*Assistant Examiner* — Jonathan M Foreman

(57) ABSTRACT

A needle assembly and delivery system for biopsying tissue of a patient includes a flexible biopsy needle, a cannula for receiving and supporting the biopsy needle, and a guide assembly which defines at least one guide assembly for receiving, guiding, and orienting the flexible biopsy needle and cannula through an angle of at least forty degrees through the needle guide assembly to a fixed orientation and position for biopsying tissue of the patient. The biopsy needle includes a sampling section which has smooth or rounded edges, a bending section which has a first circular cross-section, and a body portion proximal of the bending section which has a second circular cross-section larger than the first circular cross-section. The flexible biopsy needle, cannula, and guide assembly may be used with a biopsy ultrasound delivery system which includes an ultrasonic probe and a biopsy gun.

29 Claims, 9 Drawing Sheets

(56) References Cited

U.S. PATENT DOCUMENTS

| | | | |
|---|---|---|---|
| 5,170,793 | A | 12/1992 | Takano et al. |
| 5,181,514 | A | 1/1993 | Solomon et al. |
| 5,331,962 | A | 7/1994 | Coleman et al. |
| 5,361,768 | A | 11/1994 | Webler et al. |
| 5,368,045 | A | 11/1994 | Clement et al. |
| 5,394,878 | A | 3/1995 | Frazin et al. |
| 5,398,690 | A | 3/1995 | Batten et al. |
| 5,456,258 | A | 10/1995 | Kondo et al. |
| 5,460,179 | A | 10/1995 | Okunuki et al. |
| 5,474,072 | A | 12/1995 | Shmulewitz |
| 5,497,776 | A | 3/1996 | Yamazaki |
| 5,592,942 | A | 1/1997 | Webler et al. |
| 5,611,343 | A | 3/1997 | Wilson |
| 5,634,466 | A | 6/1997 | Gruner |
| 5,660,185 | A | 8/1997 | Shmulewitz et al. |
| 5,671,748 | A | 9/1997 | Itoi |
| 5,762,066 | A | 6/1998 | Law et al. |
| 5,769,079 | A | 6/1998 | Hossack |
| 5,810,007 | A | 9/1998 | Holupka |
| 5,842,473 | A | 12/1998 | Fenster et al. |
| 5,873,828 | A | 2/1999 | Fujio |
| 5,875,778 | A | 3/1999 | Vroegop |
| 5,931,788 | A | 8/1999 | Keen et al. |
| 5,951,489 | A | 9/1999 | Bauer |
| 5,964,707 | A | 10/1999 | Fenster et al. |
| 6,004,271 | A | 12/1999 | Moore |
| 6,036,649 | A | 3/2000 | Yuasa |
| 6,102,867 | A | 8/2000 | Dieta et al. |
| 6,149,598 | A | 11/2000 | Tanaka |
| 6,165,136 | A | 12/2000 | Nishtala |
| 6,171,249 | B1 | 1/2001 | Chin |
| 6,200,269 | B1 | 3/2001 | Lin et al. |
| 6,238,336 | B1 | 5/2001 | Ouchi |
| 6,261,234 | B1 | 7/2001 | Lin |
| 6,261,243 | B1 | 7/2001 | Burney |
| 6,315,724 | B1 | 11/2001 | Berman et al. |
| 6,390,973 | B1 | 5/2002 | Ouchi |
| 6,409,666 | B1 | 6/2002 | Ito |
| 6,419,641 | B1 | 7/2002 | Mark et al. |
| 6,447,477 | B2 | 9/2002 | Burney et al. |
| 6,485,411 | B1 | 11/2002 | Konstorum et al. |
| 6,565,588 | B1 | 5/2003 | Clement et al. |
| 6,685,648 | B2 | 2/2004 | Flaherty et al. |
| 6,689,067 | B2 | 2/2004 | Sauer et al. |
| 6,709,397 | B2 | 3/2004 | Taylor |
| 6,712,783 | B1 | 3/2004 | Jang |
| 6,884,219 | B1 | 4/2005 | Pruter |
| 7,066,889 | B2 | 6/2006 | Taylor |
| 7,171,255 | B2 | 1/2007 | Holupka et al. |
| 7,914,467 | B2 * | 3/2011 | Layman et al. ............... 600/585 |
| 7,998,132 | B2 | 8/2011 | Gregorich et al. |
| 2002/0002349 | A1 | 1/2002 | Flaherty et al. |
| 2002/0111634 | A1 | 8/2002 | Stoianovici et al. |
| 2003/0078502 | A1 | 4/2003 | Miyaki |
| 2003/0120154 | A1 | 6/2003 | Sauer et al. |
| 2003/0135119 | A1 | 7/2003 | Lee et al. |
| 2004/0030250 | A1 | 2/2004 | Stewart |
| 2004/0133111 | A1 | 7/2004 | Szczech |
| 2004/0133124 | A1 * | 7/2004 | Bates et al. ............... 600/564 |
| 2004/0204650 | A1 | 10/2004 | Taylor |
| 2005/0159676 | A1 | 7/2005 | Taylor et al. |
| 2005/0203413 | A1 | 9/2005 | Fichtinger et al. |
| 2007/0123797 | A1 | 5/2007 | Krause |
| 2008/0159606 | A1 | 7/2008 | Suri et al. |
| 2008/0161687 | A1 | 7/2008 | Suri et al. |
| 2008/0269588 | A1 | 10/2008 | Csavoy et al. |
| 2009/0048515 | A1 | 2/2009 | Suri et al. |
| 2009/0054807 | A1 * | 2/2009 | Taylor et al. ............... 600/567 |
| 2010/0305470 | A1 * | 12/2010 | Ireland ............... 600/567 |

FOREIGN PATENT DOCUMENTS

| | | |
|---|---|---|
| EP | 0504480 | 9/1992 |
| WO | WO9316641 | 9/1993 |
| WO | WO0108561 | 2/2001 |
| WO | WO03088833 | 10/2003 |

OTHER PUBLICATIONS

"Execution of Robot-Assisted Biopsies Within The Clinical Context," Rovetta et al, Journal of Image Guided Surgery, 1: 280-287, 1995.

"Transrectal Prostate Biopsy Inside Closed MRI Scanner with Remote Actuation, under Real-Time Image Guidance," Fichtinger et al, MICCAAI 2002, LNCS 2488 pp. 91-98, 2002.

"A Robotic System for Transrectal Needle Insertion into the Prostate with Integrated Ultrasound", Chad M. Schneider et al., Proceedings of the 2004 IEEE Interntational conference on Robotics & Automation, Apr. 2004, pp. 365-370.

Parker Aquasonic Clear Ultrasound Transmission Gel 8 oz *(.25L) for Ultrasonic Conductivity, EZUltrasound.com, downloaded on Apr. 27, 2010, available at http://ezultrasound.com/aquasonic8oz.aspx.

Three-Dimensional Rigid and Non-Rigid Image Registration for the Pelvis and Prostate, Baowei Fei et al, Handbook of Medical Image Analysis, 2005,, Chapter 3, pp. 103-149.

Closed-Loop Control in Fused MR-TRUS Image-Guided Prostate Biopsy, Sheng Xu et al, NIH Public Access Author Manuscript, 2008.

Registering Histological and MR Images of Prostate for Imagebased Cancer Detection, Yiqiang Zhang et al, NIH Public Access Manuscript, 26 pages, 2008.

Ergonomic Biopsy Gun, Ofer Gofrit Md,Phd, Hadasit, downloaded 04/28/10, available at www.hadasit.co.il/category/ergonomic-biopsy-gun.

Prostate Ultrasound and Biopsy, Monterey Bay Urology Association, downloaded Apr. 28, 2010, available at www.montereybayurology.com/officepro/ProstateUltrasoundandBiopsy.htm.

Stereotactic Biopsy Operation Types, GE Healthcare Product Specifications, downloaded Apr. 27, 2010, available at www.gehealthcare.com/usen/xr/mammo/products/sbiopsy_optype.html.

* cited by examiner

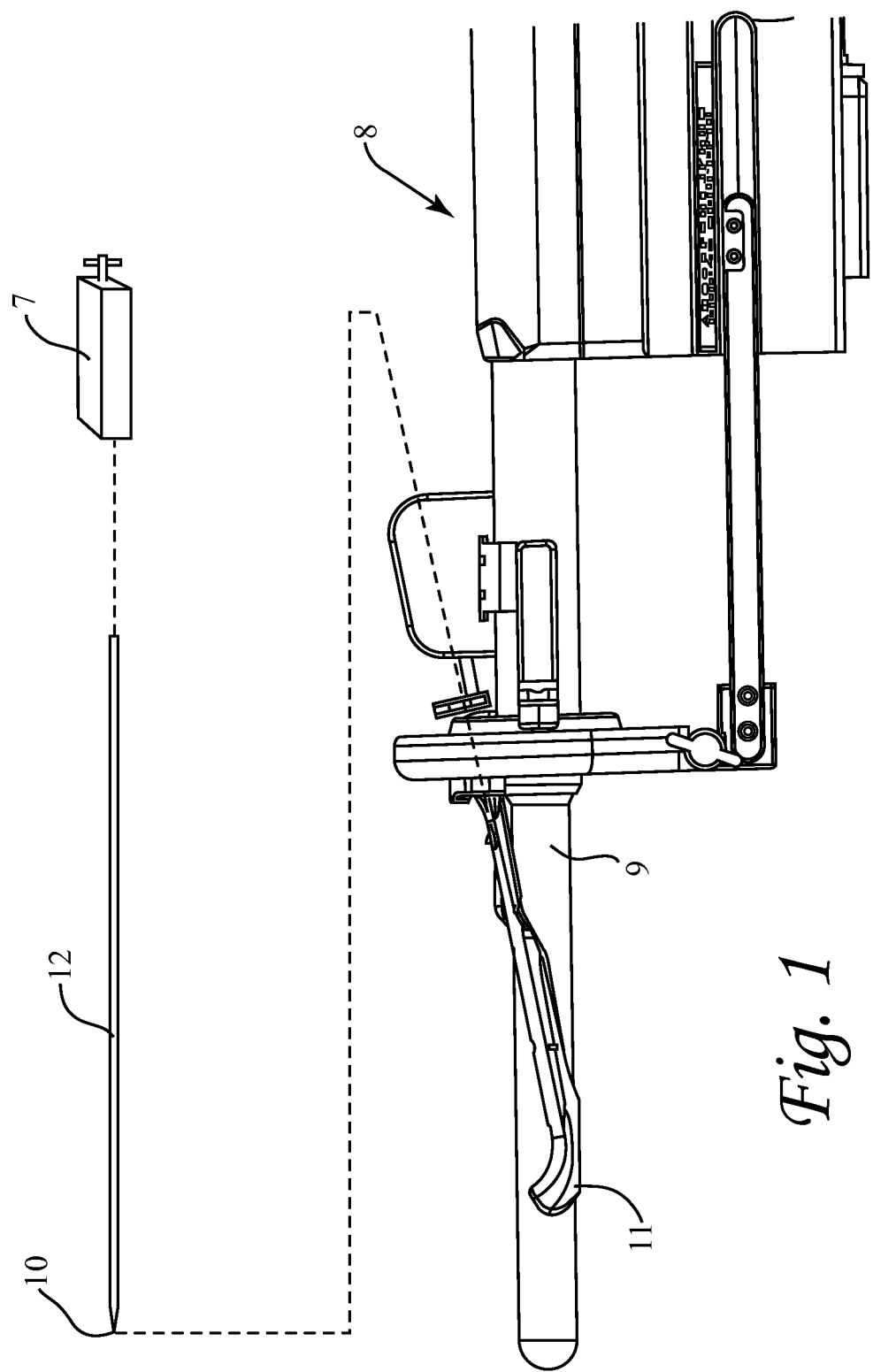

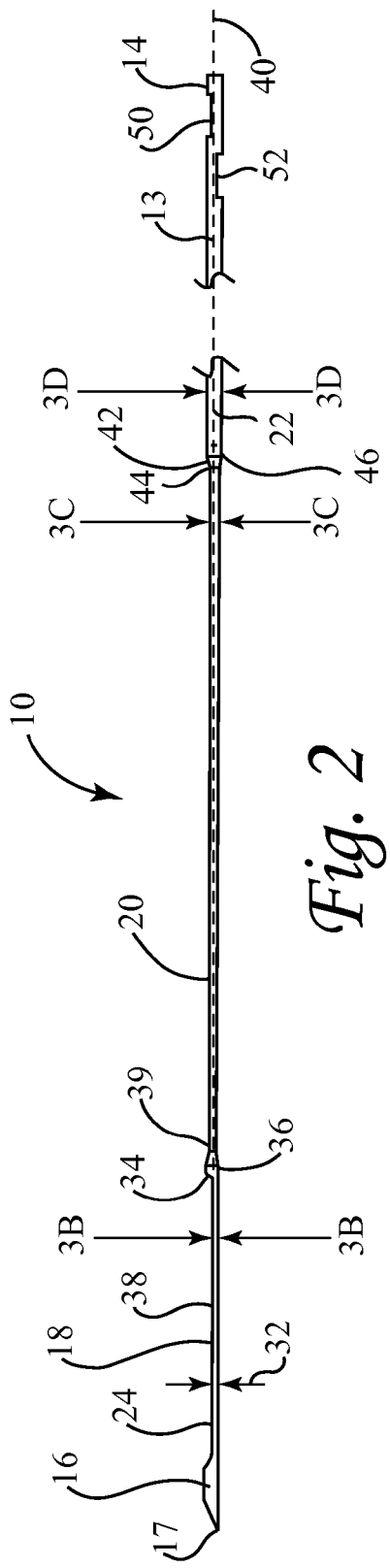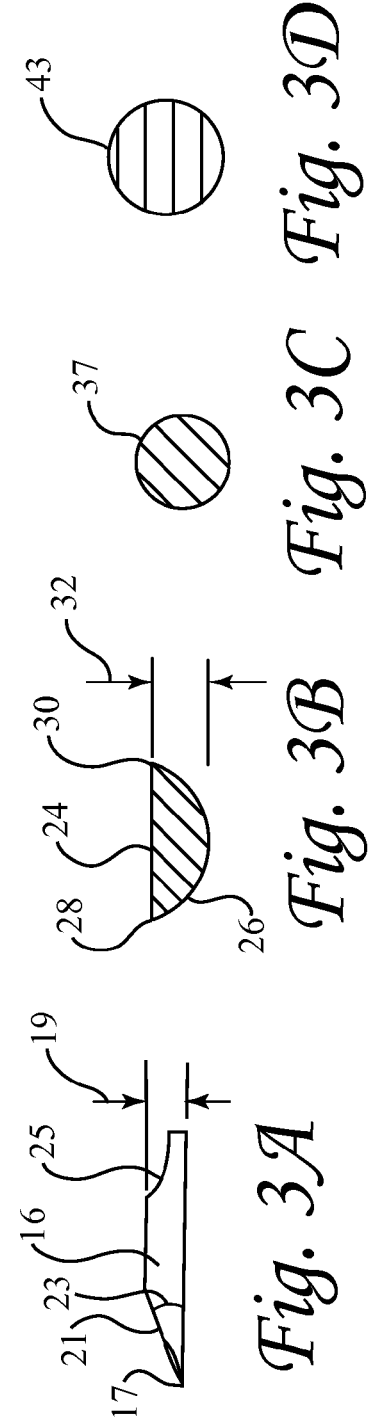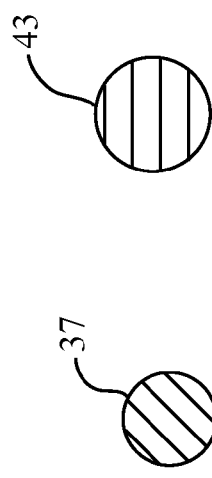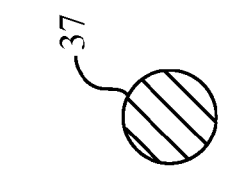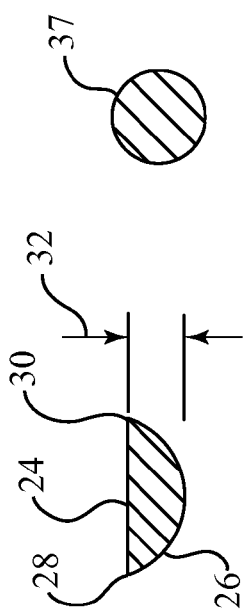

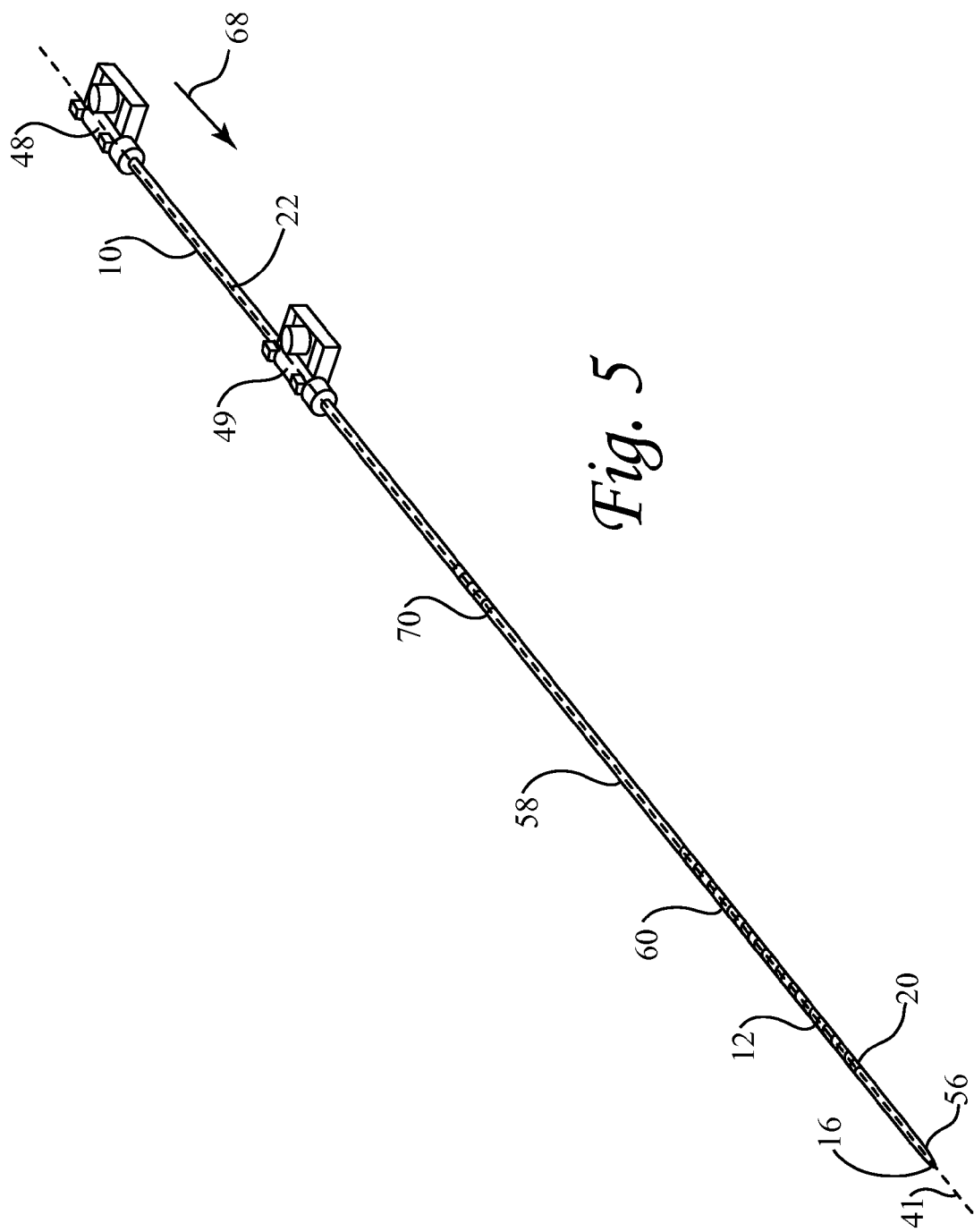

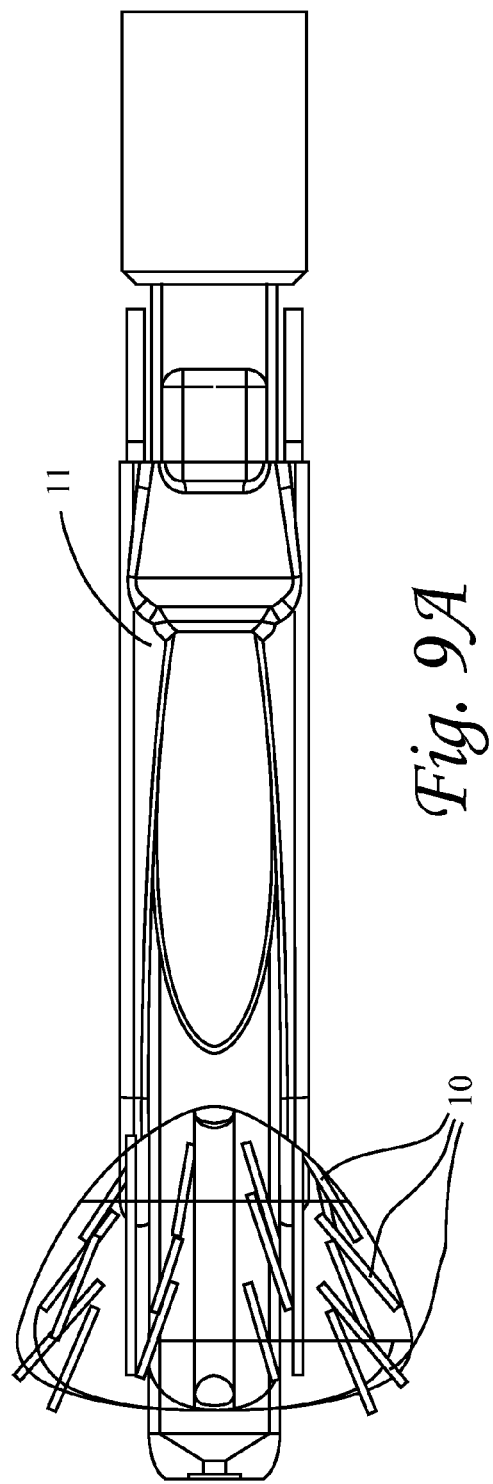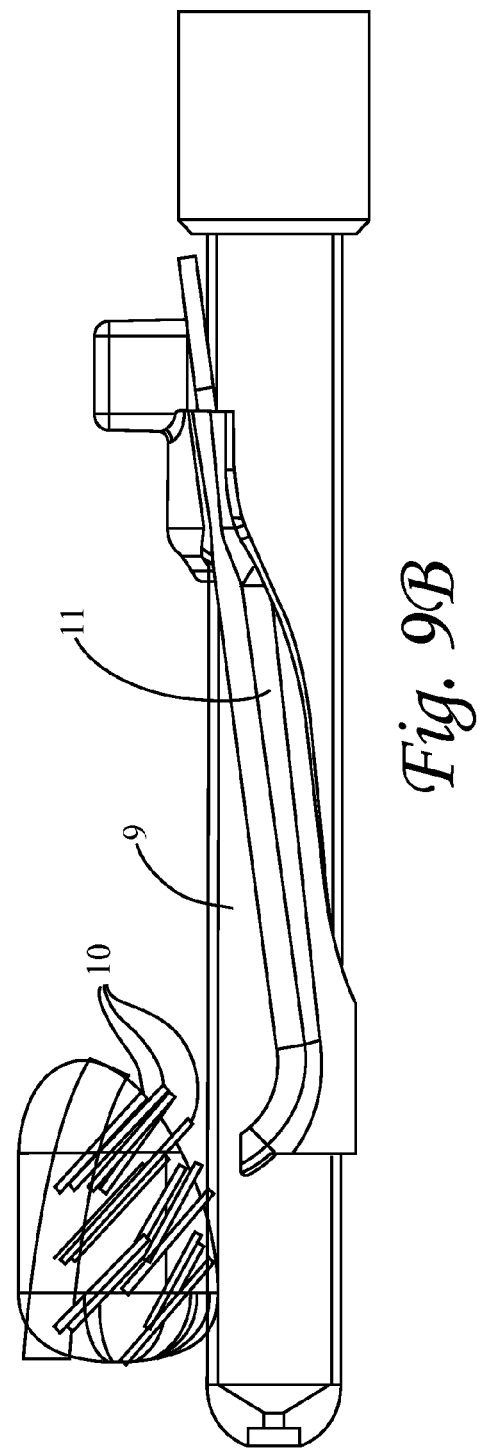

BIOPSY NEEDLE ASSEMBLY

CROSS REFERENCED TO RELATED APPLICATIONS

This application is related to U.S. Ser. No. 12/834,384, entitled "Scanning Probe", filed concurrently herewith.

BACKGROUND OF THE INVENTION

1. Field of the Invention

This invention relates broadly to spring loaded biopsy instruments, and more particularly to flexible needle assemblies for guided biopsy over straight or askew pathways.

2. State of the Art

Prostate health is a significant concern for men over the age of fifty. If prostate cancer is suspected after a physical examination of a patient or after a Prostate Specific Antigens test, then a biopsy is typically performed to collect tissue samples from the prostate for evaluation by a pathologist. Prostate tumors are small growths which can be scattered about different portions of the prostate. Thus, multiple tissue samples (e.g., typically between 9 and 18) are usually taken from the prostate during the biopsy procedure. The physician performing the biopsy is typically guided by an ultrasound device which is inserted into the rectum of the patient, a procedure known as a Transrectal Ultrasound (TRUS) Guided Prostate Biopsy. The ultrasound device includes a probe which generates images of two-dimensional slices of the prostate. In some systems, the two-dimensional images can be processed to construct a three-dimensional model of the prostate.

During a prostate biopsy procedure, a biopsy needle assembly (which includes a biopsy needle and an outer cylindrically shaped cannula which receives and supports the biopsy needle) is utilized for procuring a tissue sample. The needle assembly and cannula are typically coupled to and/or operably disposed within a spring loaded instrument (typically referred to as a biopsy gun). An ultrasonic probe is inserted into the rectum of the patient adjacent the prostate. The ultrasound probe is used to view the prostate and to provide feedback to adjust the positioning and/or depth of the probe and guide assembly in the rectum. The guide assembly is used to guide the distal end of the needle assembly through the rectal wall to a fixed position and orientation adjacent the prostate. The biopsy gun is used to advance the needle of the needle assembly into the prostate. During firing of the biopsy gun, the needle rapidly advances relative to the cannula into the prostate over a distance called the stroke length, which is typically between 15 mm to 25 mm. The needle may define a notch portion which, upon entry into the prostate, functions as a sampling area by causing tissue within the prostate to slip or prolapse into the notch. A second firing of the biopsy gun causes the cannula to advance over the exposed notch portion of the needle in the prostate. As the cannula advances over the exposed notch portion of the needle, it cuts and severs tissue surrounding the needle and traps the tissue within the notch portion, thereby capturing a tissue sample. The needle and cannula are then withdrawn from the patient with the tissue sample captured within the cannula. This process can be repeated at multiple tissue locations in the prostate.

The angle at which an ultrasonic probe and needle guide can be entered into and positioned within the rectum of a patient is limited. Standard biopsy needles known in the art are straight and do not bend during use. Flexible biopsy needles are disclosed in U.S. patent application Ser. No. 11/895,228, an example of which is shown in FIG. 9 herein. A portion of the needle of FIG. 9 is capable of being bent through an angle within guide channels of a needle guide assembly which physically deforms the needle and cannula as they pass therethrough.

The biopsy needle assemblies and firing guns can be at least partially hand operable, such as that disclosed in U.S. Pat. No. 5,368,045, which discloses a one handed biopsy needle instrument employing spring driven releasably latched stylets and cannulas capable of taking multiple specimens while the other hand of the physician is free to manipulate an ultrasound probe. U.S. Pat. No. 6,165,136 to Nishtala discloses a biopsy needle coupled to a trigger mechanism for taking a tissue sample.

SUMMARY OF THE INVENTION

The invention is directed to a needle assembly for biopsying tissue of a patient, and is preferably utilized in conjunction with a biopsy ultrasound delivery system similar to those disclosed in U.S. patent application Ser. No. 11/895,228, U.S. patent application Ser. No. 11/475,674, or U.S. patent application Ser. No. 12/834,384, which are hereby incorporated by reference in their entireties herein. The needle assembly includes an improved flexible biopsy needle and an outer cannula for receiving and supporting the biopsy needle.

The improved needle has a proximal end, a tissue piercing distal end, a sampling section proximal of the tissue piercing distal end, a bending section proximal of the sampling section, and a body portion proximal of the bending section. A cannula with a tissue piercing distal tip surrounds the needle. The bending section and body portion of the needle are both preferably formed with circular cross-sections. The bending section has a substantially smaller cross-section than that of the body portion, and a substantially longer length than that of the sampling section.

The cannula has a proximal end, a tissue piercing distal tip, and an elongate body extending between the proximal end and the second tissue piercing distal tip. The elongate body of the cannula includes a bendable portion adjacent the tissue piercing distal tip. The cannula defines a lumen which extends through the elongate body. The biopsy needle is insertable into and longitudinally translatable through the lumen of the cannula.

Prior to and during a biopsy procedure, the needle and cannula can assume a straight configuration and a bent configuration. In the straight configuration, the tissue piercing distal ends of the needle and cannula, respectively, are disposed adjacent each other, the bending section of the needle is disposed within the bendable portion of the cannula, and the bending section of the needle, the body portion of the needle, and the elongate body of the cannula are substantially straight and substantially symmetrical about a first longitudinal axis extending through the needle and cannula. In the bent configuration, the tissue piercing distal ends of the needle and cannula, respectively, are disposed adjacent each other, the bending section of the needle is disposed within the bendable portion of the cannula, and the bending section of the needle and the bendable portion of the cannula both extend through an angle of at least forty degrees, and preferably through an angle of between forty and sixty degrees.

In the preferred embodiment, the needle assembly is used in conjunction with a guide assembly which defines at least one guide channel extending between an inlet and an outlet. The inlet receives the distal end of the needle assembly (e.g., the needle and the cannula). The guide channel functions to physically bend the needle and cannula when the needle and cannula are advanced therethrough such that the distal end of the needle assembly exits the outlet of the guide channel at a desired orientation and direction. In particular, the distal section of the guide channel is curved to provide a bend angle across the distal section. When the needle assembly passes though the bend of the distal section, the distal section bends the needle and cannula such that the needle and cannula are aligned in the bent configuration with the tissue piercing distal ends of the needle and cannula disposed adjacent each other in the desired orientation and direction. In this bent configuration, the bending section of the needle is disposed within the bendable portion of the cannula, and the bending section of the needle and the bendable portion of the cannula both extend through an angle of at least forty degrees, and preferably through an angle of between forty and sixty degrees. In this manner, the needle and cannula are directed by the guide assembly in a predetermined controlled direction to facilitate adequate placement of the sampling section of the needle into the desired tissue to be sampled.

In the preferred embodiment, the sampling section of the needle is formed with a flat top surface and a rounded bottom surface which intersects the flat top surface along opposing edges on opposite sides of the sampling section. The opposing edges are preferably ground down to a smooth contour which further reduces friction between the needle and cannula, and thus the force required to advance the sampling section of the needle through the cannula, particularly through bent portions of the cannula.

In the preferred embodiment, the needle assembly and guide assembly are utilized in conjunction with a biopsy ultrasound delivery system which includes an ultrasonic probe and a biopsy gun. The needle assembly is disposed within and coupled to the biopsy gun. The probe is inserted into the rectum of the patient adjacent the prostate. The probe is used to view the prostate and to provide feedback as to the positioning and depth of the guide assembly in the patient. Once the probe and guide assembly are properly positioned within the patient, the respective distal ends of the needle and cannula are advanced together through the inlet of the guide assembly and are guided to a fixed orientation and direction at the outlet of the guide assembly.

Once the needle and cannula are in the bent configuration and the respective distal ends of the needle and cannula are disposed adjacent the prostate, the biopsy gun is fired to advance the needle from the bent configuration into the prostate of the patient. During this first firing, the sampling portion of the needle rapidly advances out of the cannula into the prostate over a stroke length which is preferably approximately equal to the length of the sampling section. A second firing of the biopsy gun causes the cannula to advance over the exposed sampling section of the needle in the prostate, trapping sample tissue therein within the notch/sampling section of the needle between the cannula and the needle. The needle and cannula are then withdrawn from the patient with the tissue sample trapped within the cannula. This process is repeated as needed.

During the biopsy procedure, the structure of the bending section of the needle facilitates bending thereof, reduces friction between the needle and cannula, and allows the needle to be distally advanced relative to the cannula and bent through a bend angle of the guide channel while the needle and cannula are in any rotational orientation relative to a center-line of the guide channel. The bending section also helps prevent the needle from binding against the cannula, especially when the cannula is spirally cut for flexibility. As a result, substantially less force is required than otherwise needed to translate the needle and cannula relative to each other during the firings of the biopsy gun. The reduced friction between the needle and cannula can also lead to increased needle and cannula velocity during their respective firings, which allows for cleaner cuts of the prostate tissue. The reliability and longevity of the needle and cannula (e.g., the needle's capability of being used numerous times within a patient) can also be improved. The improved structure of the needle also decreases manufacturing costs, reduces the number of potential failure modes during operation, and allows for reliable use in disposable, less noisy biopsy guns.

In accord with one aspect of the invention, the circular cross section of the body portion of the needle has a diameter of less than 0.04 inches, and the circular cross section of the bending section of the needle has a diameter of less than 0.03 inches.

In accord with another aspect of the invention, the cross sectional area of the bending section of the needle is at least 40 percent less than the cross sectional area of the body portion of the needle.

In accord with yet another aspect of the invention, the bending section of the needle is at least twice as long as the sampling section of the needle.

In accord with yet another aspect of the invention, the cannula defines a spiral cut and is wrapped by an outer sheath formed from PBAX.

Additional objects and advantages of the invention will become apparent to those skilled in the art upon reference to the detailed description taken in conjunction with the provided figures.

BRIEF DESCRIPTION OF THE DRAWINGS

FIG. 1 is a partially exploded view of the preferred embodiment of the biopsy needle assembly of the invention used in conjunction with a biopsy delivery system.

FIG. 2 is a broken side view of the biopsy needle of the invention.

FIG. 3A is a side view of the tissue piercing distal end of the biopsy needle of FIG. 2.

FIG. 3B is a longitudinal view of the cross section of the sampling section of the biopsy needle of FIG. 2.

FIG. 3C is a longitudinal view of the cross section of the bending section of the biopsy needle of FIG. 2.

FIG. 3D is a longitudinal view of the cross section of the body portion of the biopsy needle of FIG. 2.

FIG. 5 is a perspective schematic view of the biopsy needle, needle hub, cannula, and cannula hub of the invention in a straight configuration.

FIGS. 9A & 9B are schematic views depicting a plurality of needle paths into the prostate as guided by the guide assembly of FIG. 8 when situated in different longitudinal and rotative positions along the probe.

DETAILED DESCRIPTION OF THE PREFERRED EMBODIMENTS

Figure 4:
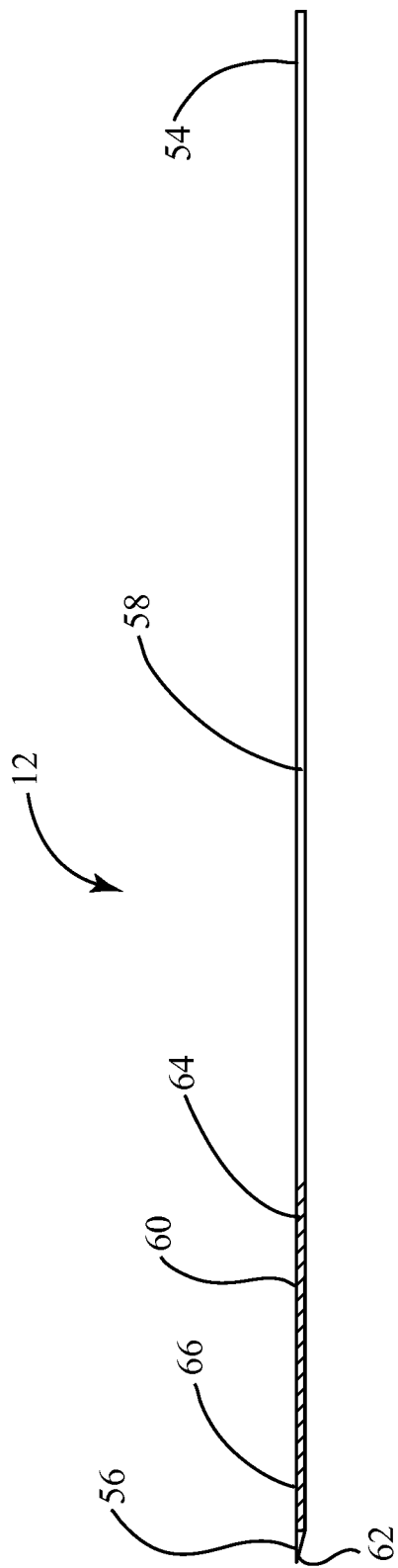
FIG. 4 is a side view of the cannula of the invention.

Turning now to FIG. 1, an improved biopsy needle 10, a cannula 12 for receiving and supporting the biopsy needle 10, and a needle guide assembly 11 are shown in conjunction with a biopsy ultrasound delivery system 8 (which includes an ultrasonic probe 9). The ultrasound delivery system may be similar to that disclosed in U.S. patent application Ser. No. 11/895,228, which is herein incorporated by reference in its entirety. The improved needle 10 and cannula 12 are preferably at least partially disposed within and coupled to a biopsy gun 7. The biopsy gun 7 and probe 9 are further discussed below with respect to the operation of the needle 10, cannula 12 and guide assembly 11 in conjunction therewith to capture a biopsy tissue sample in a patient.

The biopsy needle 10 and cannula 12 of the invention are best seen with reference to FIGS. 2-4. As most clearly shown in FIG. 2, the needle 10 includes a proximal end 14, a tissue piercing distal end 16, a sampling section 18 proximal of the tissue piercing distal end 16, a bending section 20 proximal of the sampling section 18, and a body portion 22 proximal of the bending section 20. The sampling section 18, bending section 20, and body portion 22 of the needle 10 are all preferably solidly and integrally formed with varying degrees of flexibility. The bending section 20 is preferably the most flexible portion of the needle 10.

The tissue piercing distal end 16 has a tip 17 adapted to pierce tissue. Distal end 16 has a height 19 (FIG. 3A) of appoximately 0.0395 inches (the same as body portion 22) and a distal inclined surface 21 which is inclined at an angle 23 of approximately 23°±2° and slopes downward to form the tip 17. The proximal side of the distal end 16 includes a curved portion 25 (FIG. 3A) over which the distal end 16 tapers down to the dimensions of the sampling section 18.

The sampling section 18 is preferably formed with a flat top surface 24 and a rounded bottom surface 26 (FIG. 3B) which intersects the flat top surface 24 along opposing edges 28, 30 on opposite sides of the sampling section 18. The opposing edges 28, 30 are preferably ground down to a smooth (e.g., rounded) contour and free of any burrs in order to reduce friction when the needle 10 is disposed inside of the cannula 12. This reduction in friction reduces the force necessary to translate the needle 10 relative to the cannula 12 during the biopsy procedure as further discussed below. In one embodiment, the sampling section 18 is approximately 0.782 inches in length, and preferably has a height 32 between 0.017 inches and 0.020 inches.

A first step portion 36 is provided between the proximal end 34 of the sampling section 18 and the distal end 39 of the bending section 20. The first step portion 36 provides some rigidity to the needle 10 between the flexible sampling and bending sections 18, 20, and includes a cross sectional area which is larger than that of the sampling section 18 and that of the bending section 20, but not larger than the cross sectional area of the body portion 22. The distal side of the first step portion 36 preferably has a cross sectional diameter approximately equal to the height 19 of the distal end 16, and slightly less than the inside diameter of the cannula 12 to facilitate cutting and shearing a tissue sample in the patient as the cannula 12 is advanced relative to the exposed sampling section 18 of the needle 10 in the tissue as further discussed below.

It will be appreciated that the curved portion 25 of the distal end 16, the top surface 24 of the sampling section 18, and the distal side of the first step portion 36 together define a notch or recess 38 across the length of the sampling section 18 for capturing tissue which passes over the stylet 16.

The bending section 20 of the needle 10 extends from the proximal side of the first step portion 36, and is preferably formed with a cylindrical shape and a circular cross-section 37 (FIG. 3C) symmetrical about the longitudinal axis 40 (FIG. 2) extending therethrough. The longitudinal axis 40 is considered to be the central axis of the bending section 20 and body portion 22 of the needle 10, whether in a straight or bent configuration (further discussed below). The cross-section 37 of the bending section 20 is preferably substantially smaller than the cross-section 43 (FIG. 3D) of the body portion 22, and substantially longer in length than the sampling section 18. In particular, in one embodiment, the diameter of the bending section 20 is 0.026±0.001 inches, and its length is preferably between 2.00 inches and 2.03 inches.

A second step portion 42 is provided between the proximal end 44 of the bending portion 20 and the distal end 46 of the body portion 22. In one embodiment, the second step portion 42 is conically shaped, and increases in diameter between the bending and body portions 20, 22. The second step portion 42 provides a smooth conical transition between the bending and body portions 20, 22, and allows for smooth translational sliding of the needle 10 within the spirally cut cannula 12.

The body portion 22 extends from the proximal side of the second step portion 42, and is also preferably formed with a cylindrical shape. The body portion 22 also preferably has a circular cross-section 43 (FIG. 3D) which is preferably symmetrical about the longitudinal axis 40. Thus, the bending section 20 and body portion 22 are disposed adjacent each other on opposite sides of the second step portion 42, but share the common longitudinal axis 40. In one embodiment, the body portion 22 has a diameter of preferably 0.0395±0.0003 inches and a length of between eight to eight and a half inches.

It will be appreciated that the diameter ranges listed above for the bending section 20 and body portion 22 correspond to roughly a 53% to 61% reduction in the cross sectional area of the bending section 20 relative to the body portion 22. It is preferred that the reduction in cross sectional area be in the range of 40%-60%.

The proximal end 14 of the needle 10 includes a ground section 13 (FIG. 2) which couples to a needle hub 48 (FIG. 5) via any suitable coupling means known in the art. For example, the ground section 13 may define female recesses 50, 52 which mechanically couple to corresponding male surfaces (not shown) within the needle hub 48.

The proximal end 14, tissue piercing distal end 16, sampling section 18, bending section 20, body portion 22, and first and second step portions 36, 46 of the needle 10 are preferably integrally formed and made from nitinol, though other flexible materials may be utilized.

As further discussed below, the structure of the bending section of the needle 10 reduces friction in the needle assembly between the needle and cannula, facilitates advancement of the needle 10 and cannula 12 through a given bend angle of the guide assembly 11 at any rotational orientation relative to the center-line of the guide assembly 11, helps prevent failure of the needle assembly, reduces manufacturing costs, increases the reliability and longevity of the needle 10, and allows for cleaner cuts of the tissue when the needle is fired from a biopsy gun.

Turning now to FIG. 4, the cannula 12 has a proximal end 54, a tissue piercing distal end 56, and an elongate body 58 extending between the proximal end 54 and tissue piercing distal end 56. In one embodiment, the elongate body 58 of the cannula 12 is approximately eight to eight and a half inches long and includes a bendable portion 60 adjacent the second tissue piercing distal end 56 which is approximately three to three and a half inches in length. The cannula 12 is preferably 18 gage thin wall tubing and defines a lumen 62 which extends through the elongate body 58 and the second proximal and distal ends 54, 56. The lumen has a diameter of approximately 0.042 inches±0.001. The outer diameter of the cannula is approximately 0.05 inches. The cannula is preferably surrounded by a flexible outer sheath 66 formed from a flexible, heat shrinkable, polymeric protective coating or material such as PEBAX® or other suitable material known in the art. In one embodiment, the outer diameter of the cannula 12 with the surrounding sheath 66 is approximately 0.054. The cannula 12 and lumen 62 are thus sized to receive the entire biopsy needle 10 such that the entire biopsy needle 10 is longitudinally translatable through the lumen 62 of the cannula 12. The proximal end 54, tissue piercing distal end 56, and elongate body 58 of the cannula 12 are preferably made from stainless steel, though other flexible materials may be utilized.

In the preferred embodiment, the bendable portion 60 of the elongate body 58 of the cannula 12 defines a spiral cut 64 (e.g., a helical cut) for facilitating bending thereof. In the preferred embodiment, the spirally cut bendable portion 60 is wrapped by the flexible outer sheath 66. The sheath 66 functions to help hold together and support the spirally cut bendable portion 60 of the cannula 12, and adds about 0.004 inches to the outer diameter of the cannula 12 as discussed above.

Turning to FIG. 5, the biopsy needle 10 is affixed to the needle hub 48 and the cannula 12 is affixed to a cannula hub 49. The needle hub 48 is movable in the direction of the arrow 68 while the cannula hub 49 is held fixed, which translates the needle 10 relative to and inside of the cannula 12. Alternatively, the cannula hub 49 may be longitudinally translated to move the cannula 12 proximally or distally relative to the needle 10. The hubs 48, 49 attach the needle 10 and cannula 12 to respective pins on the biopsy gun 7 which are attached to respective springs for firing the needle 10 and cannula 12 as further discussed below. The needle 10 and cannula 12 may alternatively be attached directly to springs in a disposable gun to perform the same operation. The cannula 12 may be provided with depth markings 70 to provide a visual indication to the physician of how far the cannula 12 has been inserted into the patient.

Figure 6A:
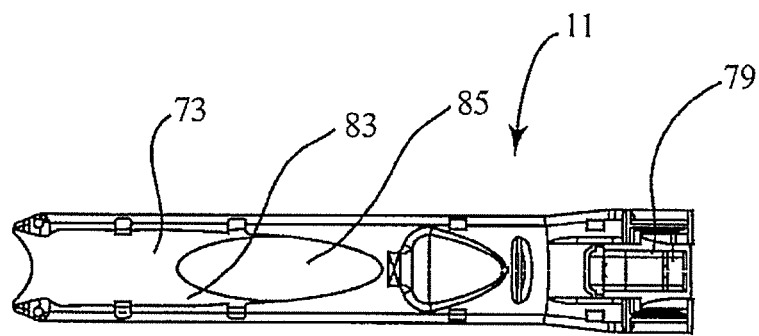
FIG. 6A is a top view of the guide assembly of the invention.
Figure 6B:
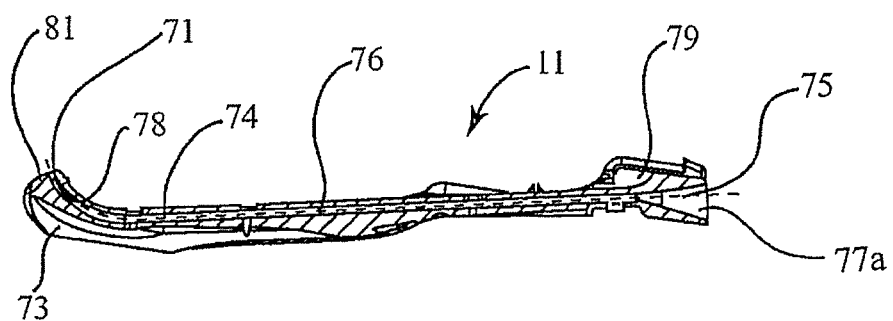
FIG. 6B is a side view of the guide assembly of FIG. 6A.

Turning to FIGS. 6A and 6B, the guide assembly 11 includes a housing 73 which defines passageways 76 on opposite sides thereof. The passageways 76 include inlets 75 at the proximal end of the housing 73 on opposite sides thereof, and outlets 81 at the distal end of the housing 73 on opposite sides thereof. The passageways 76 extend between and in open communication with the inlets 75 and outlets 81 on opposite sides of the housing 73. Hollow guide tubes 74 (FIG. 6B) are preferably provided within each passageway 76 to provide guide channels through which the needle 10 and cannula 12 are advanced.

Figure 6C:
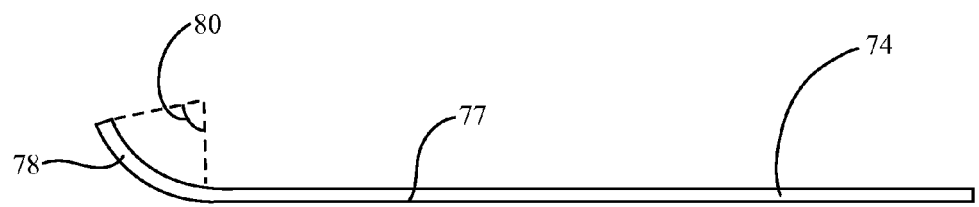
FIG. 6C is a side view of the guide tube of the guide assembly of FIG. 6B.

The inlets 75 have a wide entrance 77a to facilitate easy insertion of the needle 10 and the cannula 12 into the guide assembly 11, and taper in the distal direction to the dimensions of the guide tubes 74 to guide the needle 10 and the cannula 12 into the guide tubes 74. As shown in FIG. 6C, the guide tubes 74 each include a proximal straight portion 77 and a distal curved portion 78, and define a center-line 71 (FIG. 6B) extending through the straight and distal curved portions 77, 78. The straight portion 77 may be oriented horizontal relative to the longitudinal axis of the guide assembly 11, or sloped downward in the distal direction. In one embodiment, the bottom surface of the curved portion 78 curves upward approximately between 0.506 inches and 0.516 inches from the straight portion 77 through an angle 80 of at least 45° and preferably at least 72° (e.g. circumscribes an angle of 72°). The guide tubes 74 have an approximate inner diameter of 0.071 inches and an outer diameter of 0.095 inches. The housing 73 and the guide tubes 74 are preferably made from a plastic, metal, or other suitable material. The guide tubes 74 are preferably rigid so as to maintain their shape, and preferably have low static and kinetic coefficients of friction so as to minimize friction with the needle 10 and cannula 12.

It will be appreciated that the guide tubes 74 function to physically bend the needle 10 and the cannula 12 when the needle 10 and the cannula 12 are advanced therethrough such that the distal ends 16, 56 of the needle 10 and the cannula 12 exit the outlet 81 of the guide assembly 11 at a desired orientation and direction. In particular, when the needle 10 and the cannula 12 pass through the curved portion 78, the curved portion 78 bends the needle 10 and the cannula 12 such that the needle 10 and the cannula 12 can be aligned in the bent configuration with their tissue piercing distal ends 16, 56 disposed adjacent each other, the bending section 20 of the needle 10 disposed within the bendable portion 60 of the cannula 12, and the bending section 20 of the needle 10 and the bendable portion 60 of the cannula 12 both extending through an angle of at least forty degrees, preferably between forty and sixty degrees, and most preferably at approximately forty-five degrees relative to the longitudinal axis of the probe 9 to which the guide assembly 11 is coupled (further discussed below). As the inside diameter of the guide tube 74 is preferably considerably larger than the outside diameter of the needle 10 (e.g., 0.071 inches compared to 0.054 inches), the needle 10 loosely fits inside the guide tube 74 and bends through an angle which is approximately seventeen degrees less than the curved portion 78 of the guide tube 74. As discussed above, the typically desired needle exit angle is forty-five degrees relative to the longitudinal axis of the probe 9. The straight portion 77 of the guide tubes 74 of the guide assembly 11 is preferably sloped downward at a ten degree angle relative to the probe 9 when positioned on the probe 9 as further discussed below. Thus, it will be appreciated that the needle 10 preferably bends through an angle of approximately 55 degrees in order to extend from the guide assembly 11 at an angle of 45 degrees relative to the probe axis (e.g., 72°−17°−10°=45°). However, the guide assembly 11 may alternatively be designed to produce a higher needle exit angle. In this manner, the needle 10 and the cannula 12 are directed by the guide assembly 11 in a predetermined controlled direction to facilitate adequate placement of the sampling section 18 of the needle 10 into the desired tissue to be sampled.

The housing 73 of the guide assembly 11 also preferably includes a clip section 79 and a curved bottom surface 83 which defines an oval shaped hole 85. The clip section 79, curved bottom surface 83, and hole 85 are constructed to allow the guide assembly 11 to be attached to the probe 9, preferably with the guide channels 76 disposed on opposite sides of the probe 9, for insertion into the rectum of a patient. In particular, the distal end of the probe 9 is inserted through the oval shaped hole 85 defined by the housing 73, and the clip section 79 attaches to a guide collar on the probe 9. The guide collar is movable relative to the probe 9 through various angles and depths specified by a computer (not shown) for each sample to provide positioning of the outlets 81 of the guide assembly 11 relative to the prostate. The probe and guide collar are operably coupled to the computer (not shown) which provides location information so that the guide collar and attached guide assembly 11 can be manually rotated or longitudinally translated to predetermined locations.

Figure 7:
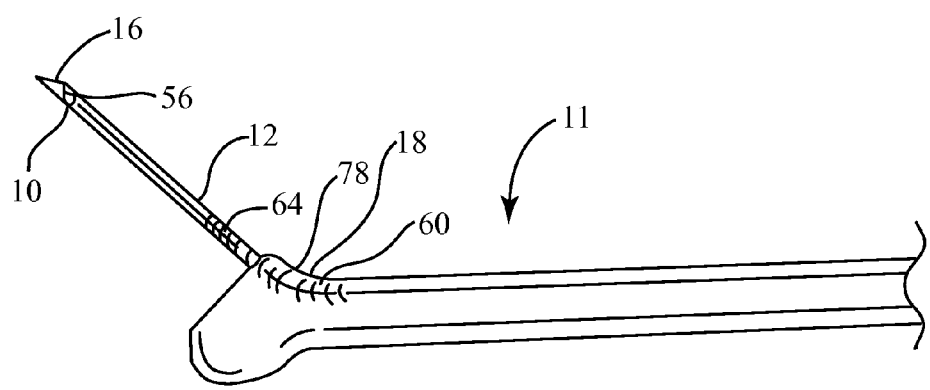
FIG. 7 is a side view of the biopsy needle and cannula extending through the guide assembly in a bent configuration.

Prior to and during a biopsy procedure, the needle 10 and cannula 12 can assume a straight configuration (e.g., such as that shown in FIG. 5) and a bent configuration (e.g., such as that shown in FIG. 7). In the straight configuration, the first and second tissue piercing distal ends 16, 56 of the needle 10 and cannula 12, respectively, are disposed adjacent each other, the bending section 20 of the needle 10 is disposed within the spirally cut bendable portion 60 of the cannula 12, and the bending section 20 of the needle 10, the body portion 22 of the needle 10, and the elongate body 58 of the cannula 12 are substantially straight and substantially symmetrical about a longitudinal axis 41 (FIG. 5) extending through the needle 10 and cannula 12.

Inserting the needle 10 and the cannula 12 in the straight configuration through the tapered inlet 75 (FIG. 6B) of the guide assembly 11, into the straight portion 77 of the guide tube 74, and up to and through the curved portion 78 (FIGS. 6B, 6C), bends the needle 10 and the cannula 12 such that the needle 10 and the cannula 12 can be aligned in the bent configuration of FIG. 7 in any arbitrary rotational orientation about the center-line 71 of the guide tubes 74.

Turning to FIG. 7, the needle 10 and cannula 12 are shown in the bent configuration after being advanced together through the curved portion 78 of the guide assembly 11. In this bent configuration, the first and second tissue piercing distal ends 16, 56 of the needle 10 and cannula 12, respectively, are disposed adjacent each other, the bending section 18 of the needle 10 is disposed within the bendable portion 60 of the cannula 12, and the bending section 18 of the needle 10 and the bendable portion 60 of the cannula 12 both extend through (e.g., circumscribe) an angle of at least forty degrees.

Figure 8:
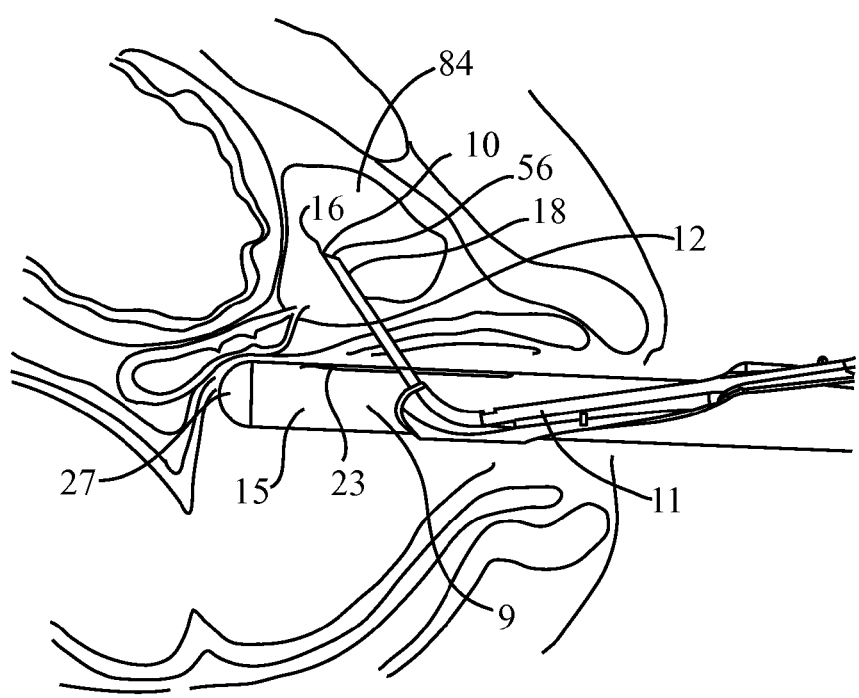
FIG. 8 is a schematic view of the biopsy needle, cannula, and guide assembly mounted on a side-fired probe and used to biopsy the prostate of a patient.
Figure 10:
FIG. 10 is a broken side view of a flexible biopsy needle known in the art.

Turning to FIGS. 1 and 8, the needle assembly (e.g. the needle 10 and the cannula 12) and the guide assembly 11 are preferably utilized in conjunction with a biopsy ultrasound delivery system 8 which includes an ultrasonic probe 9 and a biopsy gun 7. The needle 10 and the cannula 12 are preferably at least partially disposed within and coupled to the biopsy gun 7. It will be appreciated that the methodology and additional equipment utilized can be in accordance with various biopsy procedures, including, for example, the prostate biopsy procedure described in U.S. patent application Ser. No. 11/895,228 and U.S. patent application Ser. No. 12/834,384, which are incorporated herein by reference in their entirety. The probe 9 includes an elongate outer housing 15, a tip 27, and an imaging window 23. The elongate housing 15 of the probe 9 preferably includes a portion which is shaped to mate with the curved bottom surface 83 and the hole 85 of the guide assembly 11. The probe 9 is inserted into the rectum of the patient adjacent the prostate 84 as shown in FIG. 8. The probe 9 is used to view the prostate 84 and to provide feedback as to the positioning and depth of the probe 9 and guide assembly 11 during the biopsy procedure.

The guide assembly 11 is preferably attached to the guide/index collar of the probe 9, and slides radially and axially on the probe 9. Alternatively, the guide assembly 11 may be fixed to the probe 9. The guide assembly 11 is preferably disposed proximal of the imaging window 23 such that ultrasonic images of the prostate 84 can be received through the imaging window 23, unobstructed by the guide assembly 11. The guide assembly 11 may also be situated such that the guide channels 76 are disposed on opposite sides of the probe housing 15.

Once the probe 9 and the guide assembly 11 are properly positioned within the patient, the respective distal ends 16, 56 of the needle 10 and the cannula 12 are then advanced together through the inlet 75 of the guide assembly 11 and are guided to a fixed orientation and direction at the outlet 81 of the guide assembly 11 to place the needle 10 and cannula 12 in the bent configuration within the patient adjacent the prostate. The circular cross section 37 of the bending section 20 of the needle 10 allows both the needle 10 and the cannula 12 to be positioned in any rotational orientation relative to the center-line 71 of the guide tube 74 of the guide assembly 11 for deployment into tissue.

Once the needle 10 and the cannula 12 are in the bent configuration and the respective distal ends 16, 56 of the needle 10 and cannula 12 are disposed adjacent the prostate 84, the biopsy gun 7 is fired to advance the needle 10 from the bent configuration into the prostate 84 of the patient (FIG. 8). During this first firing, the sampling portion 18 of the needle 10 rapidly advances out of the cannula 12 into the prostate 84 over a stroke length which is preferably approximately equal to the length of the sampling section 18 (FIG. 8). It will be appreciated by those skilled in the art that ground down edges on opposite sides of the sampling section 18 reduce friction between the sampling section 18 of the needle 10 and the cannula 12 and prevents the sampling section 18 of the needle 10 from jamming within the spiral cut 64 of the cannula 12. It will also be appreciated that the longer length and smaller circular cross section of the bending section 18 of the needle 10 relative to the lumen 62 of the cannula 12 (which needs to be large enough to accommodate the larger body portion 22 of the needle 10) significantly reduces friction as the bending section 20 of the needle 10 translates relative to the cannula 12 inside the curved portion 78 of the guide tube 74 of the guide assembly 11 when the needle 10 is advanced distally from the bent configuration. The smaller circular cross section 37 of the bending section 20 of the needle 10 allows the needle 10 to be easily bent in any direction from any rotational orientation about the center-line 71 of the guide tube 74 of the guide assembly 11 (FIG. 6B) relative to the curved portion 78 (FIG. 6B) of the guide tube 74 of the guide assembly 11. Thus, a successful distal firing of the needle 10 which advances the needle's 10's bending section 20 through the curved portion 78 of the guide tube 74 of the guide assembly 11 is not contingent on the needle 10 having a particular rotational orientation within the curved portion 78 of the guide tube 74 of the guide assembly 11 (as has sometimes been the case when using the bendable needle of U.S. patent application Ser. No. 11/895,228). Instead, the needle 10 of the present invention can be placed in or advanced to a bent configuration with any rotational orientation relative to the centerline 71 of the curved portion 78 of the guide tube 74 of the guide assembly 11. The reduced friction generated in the needle assembly due to the small circular cross section 37 of the bending section 20 and additionally the rounded bottom surface 26 of the sampling section 18 of the needle 10 results in a faster needle velocity at the distal end 56 of the cannula 12 during the first firing of the biopsy gun 7. A faster needle velocity allows for a cleaner cut of the tissue.

Bench testing has revealed that the longitudinally directed force (measured with a force transducer) required to distally advance the needle 10 relative to the cannula 12 is significantly reduced relative to the needle of application Ser. No. 11/895,228, especially when the needle assembly is in a bent configuration, and regardless of the rotational orientation of the needle 10 relative to the guide assembly 11. In particular, a nitinol needle 10 with the dimensions discussed above requires a maximum force of between seven and fifteen ounces to distally advance it from the bent configuration relative to the cannula 12 when the needle 10 is moved at bench test speeds. With respect to prior art needles, and more specifically, the bendable needle of U.S. application Ser. No. 11/895,228, bench tests reveal that forces above twenty-five ounces are generally associated with failure when used with biopsy guns, that needles which test under twenty ounces of bench test force function properly with various biopsy guns such as the Manan gun (sold by Manan Medical Products, Wheeling, Ill.), and that needles which test under fifteen ounces of bench test force function properly with the disposable Inrad gun (sold by Inrad, Inc., Kentwood, Mich.). The present needle assembly achieves a significant reduction from the bench test force which was required when using the bendable needles of U.S. patent application Ser. No. 11/895,228, which required at least sixteen and generally twenty to thirty ounces of longitudinally directed force to be applied to the needle to advance it from the bent configuration relative to the cannula.

As standard biopsy guns 7 fire biopsy needles at very high speeds, which increases the total friction between the needle and the cannula, it will be appreciated that the reduction in friction during a standard biopsy procedure caused by the improved needle 10 is significant, and dramatically reduces the force necessary to advance the needle 10 relative to the cannula 12. The needle 10 is thus more reliable than prior art needles, especially if used with disposable biopsy guns.

A second firing of the biopsy gun 7 causes the cannula 12 to fire and advance over the exposed sampling section 18 of the needle 10 in the prostate 84, capturing sample tissue therein between the cannula 12 and the needle 10. It will be appreciated that the friction level generated from this second firing of the biopsy gun 7 is comparable to the friction level generated from the first firing of the biopsy gun 7, the difference being that the cannula 12 now slides over the needle 10. The advantages (e.g., reduction in friction) during the second firing of the biopsy gun 7 results in the same advantages discussed above with respect to the first firing, such as faster cannula velocity and a cleaner cut of the tissue. The needle 10 and cannula 12 are then withdrawn from the patient with the tissue sample captured within the cannula 12, and the process is repeated as needed. The reduction in friction and decreased number of failure modes of the needle assembly improves the reliability and longevity of the needle assembly (e.g., facilitates its use numerous times within a given patient to capture a plurality of samples).

It is also noted that the improved structure of the sampling and bending sections 18, 20 decrease manufacturing costs. For example, manufacturing the flat sampling and bending sections of the needle of application Ser. No. 11/895,228 required a highly expensive manufacturing procedure known as electrical discharge machining (EDM). The round bottom surface 26 of the sampling section 18 and round circular cross section 37 of the bending section 20 of the present needle 10 allow the needle 10 to be manufactured with a simple grinder wheel having a preformed edge.

It will be appreciated that various biopsy guns, probes, and delivery mechanisms may be utilized in conjunction with the needle 10, cannula 12, and guide assembly 11. The biopsy gun 7 can be at least partially hand operable, such as that disclosed in U.S. Pat. No. 5,368,045. For example, the biopsy gun 7 may include finger displaceable means (e.g., thumb actuated slide-switches) for selective loading of firing springs and/or latches for selectively holding the firing springs in a compressed state. The needle 10 and cannula may be manually loaded separately but fired sequentially with a single button. Such a configuration gives a physician one free hand to manipulate an ultrasound probe. The biopsy gun 7 may also be coupled to a trigger mechanism in a manner such as that disclosed in U.S. Pat. No. 6,165,136 to Nishtala. For example, the biopsy gun 7 may include a user manipulatable dial to adjust the cannula 12 relative to the needle 10 and to fire the needle 10 and cannula 12.

It will also be recognized that if the angle through which the needle 10 extends relative to the probe axis is greater than forty-five degrees, then the sample will be taken from a more vertical orientation of the sampling section 18 of the needle 10. A more vertical orientation of the sampling section 18 makes tissue in certain parts of the prostate 84 easier to target and sample. Conversely, the needle 10 can be oriented at an angle of less than forty-five degrees relative to the probe axis as depicted in FIGS. 9A and 9B. The exit angle of the needle 10 should be consistent and known so that the computer can take it into account when calculating its own biopsy pattern and target locations.

There have been described and illustrated herein several embodiments of a needle assembly and system for biopsying tissue in a patient. While particular embodiments of the invention have been described, it is not intended that the invention be limited thereto, as it is intended that the invention be as broad in scope as the art will allow and that the specification be read likewise. Thus, while particular dimensions, orientations, angles, shapes, and materials for a needle, cannula, guide assembly, and a biopsy delivery system which includes a probe and a biopsy gun have been disclosed, it will be appreciated that other dimensions, orientations, angles, shapes, and materials may be used as well. In addition, while particular straight and bent configurations of a needle assembly have been disclosed, it will be understood that other straight and bent configurations can be utilized. Also, while the needle, cannula, and biopsy delivery system have been disclosed for biopsying the prostate of a patient, it will be recognized that that the needle, cannula, and biopsy delivery system can be used for biopsying tissue of other organs or other parts of the body. It will therefore be appreciated by those skilled in the art that yet other modifications could be made to the provided invention without deviating from its spirit and scope as claimed.

What is claimed is:

1. A needle assembly for biopsying tissue of a patient, the needle assembly comprising:

a flexible biopsy needle having a proximal end, a tissue piercing distal end, a sampling section proximal of said tissue piercing distal end of said needle, said sampling section having a non-circular cross section, a bending section proximal of said sampling section, said bending section having a first circular cross-section, and a body portion proximal of said bending section, said body portion having a second circular cross-section larger than said first circular cross-section; and a cannula having a proximal end, a tissue piercing distal end, and an elongate body extending between said proximal end and said tissue piercing distal end of said cannula, said elongate body including a bendable portion adjacent said tissue piercing distal end of said cannula, said cannula defining a lumen through said elongate body and said tissue piercing distal end of said cannula, said biopsy needle insertable through said lumen of said cannula, wherein said needle assembly is configurable to an initial straight configuration in which said tissue piercing distal ends of said needle and said cannula are disposed adjacent each other, said bending section of said needle is disposed within said bendable portion of said cannula, and said bending section of said needle, said body portion of said needle, and said elongate body of said cannula are substantially straight and substantially symmetrical about a longitudinal axis extending through said needle assembly, and wherein said needle assembly is configurable to a bent configuration in which said tissue piercing distal ends of said needle and said cannula are disposed adjacent each other, said bending section of said needle is disposed within said bendable portion of said cannula, and said bending section of said needle and said bendable portion of said cannula extend through an angle of at least forty degrees.

2. The needle assembly according to claim 1, wherein: said bending section of said needle and said bendable portion of said cannula extend through an angle of at least fifty degrees.

3. The needle assembly according to claim 1, wherein: said second circular cross-section has a diameter of less than 0.04 inches.

4. The needle assembly according to claim 1, wherein: said first circular cross-section has a diameter of less than 0.03 inches.

5. The needle assembly according to claim 1, wherein: said bending section of said needle is at least twice as long as said sampling section of said needle.

6. The needle assembly according to claim 1, wherein: said sampling section of said needle has a flat top surface and a rounded bottom surface, said flat top surface and said rounded bottom surface intersecting along opposing edges on opposite sides of said sampling section.

7. The needle assembly according to claim 6, wherein: said opposing edges of said sampling section are ground to a smooth contour.

8. The needle assembly according to claim 1, wherein: said bendable portion of said cannula defines a spiral cut for facilitating bending of said bendable portion.

9. The needle assembly according to claim 8, further comprising:
a flexible sheath surrounding said spiral cut bendable portion of said cannula for supporting said bendable portion.

10. The needle assembly according to claim 1, wherein: said tissue piercing distal end, said sampling section, said bending section, and said body portion of said needle are made from nitinol.

11. The needle assembly according to claim 1, wherein: said first circular cross-section has a first area, said second circular-cross section has a second area, and said first area is at least 40 percent less than said second area.

12. The needle assembly according to claim 11, wherein: said first area is at least 55 percent less than said second area.

13. A needle assembly for biopsying tissue of a patient, the needle assembly comprising:
a flexible biopsy needle having a proximal end, a tissue piercing distal end, a sampling section proximal of said tissue piercing distal end of said needle, said sampling section having a non-circular cross section, a bending section proximal of said sampling section, said bending section having a first circular cross-section, and a body portion proximal of said bending section, said body portion having a second circular cross-section larger than said first circular cross-section; and
a cannula having a proximal end, a tissue piercing distal end, and an elongate body extending between said proximal end and said tissue piercing distal end of said cannula, said elongate body including a bendable portion adjacent said tissue piercing distal end of said cannula, said cannula defining a lumen through said elongate body and said tissue piercing distal end of said cannula, said biopsy needle insertable through said lumen of said cannula,
wherein said lumen of said cannula defines an inside diameter of said cannula, said needle includes a step portion between said sampling section and said bending section of said needle, and said step portion has a cross sectional diameter less than said inside diameter of said cannula.

14. A needle assembly for biopsying tissue of a patient, the needle assembly comprising:
a flexible biopsy needle having a proximal end, a tissue piercing distal end, a sampling section proximal of said tissue piercing distal end of said needle, a bending section proximal of said sampling section, and a body portion proximal of said bending section; and
a cannula having a proximal end, a tissue piercing distal end, and an elongate body extending between said proximal end and said tissue piercing distal end of said cannula, said elongate body including a bendable portion adjacent said tissue piercing distal end of said cannula, said cannula defining a lumen through said elongate body and said tissue piercing distal end of said cannula, said biopsy needle insertable through said lumen of said cannula,
wherein said needle assembly is configurable to a bent configuration in which said tissue piercing distal ends of said needle and said cannula are disposed adjacent each other, said bending section of said needle is disposed within said bendable portion of said cannula, said bending section of said needle and said bendable portion of said cannula extend through an angle of at least forty degrees, and said biopsy needle is distally advanceable relative to said cannula from said bent configuration by application of a force to said needle, said force no more than 18 ounces.

15. The needle assembly according to claim 14, wherein: said force is no more than 10 ounces.

16. A needle biopsy system for biopsying tissue of a patient, the needle biopsy system comprising:
a flexible biopsy needle having a proximal end, a tissue piercing distal end, a sampling section proximal of said tissue piercing distal end of said needle, a bending section proximal of said sampling section, said bending section having a first circular cross-section, and a body portion proximal of said bending section, said body portion having a second circular cross-section larger than said first circular cross-section;
a cannula having proximal end, a tissue piercing distal end, and an elongate body extending between said proximal end and said tissue piercing distal end of said cannula, said elongate body including a bendable portion adjacent said tissue piercing distal end of said cannula, said cannula defining a lumen through said elongate body and said tissue piercing distal end of said cannula, said biopsy needle insertable through said lumen of said cannula; and
a guide assembly which defines at least one guide channel for receiving, guiding, and orienting said flexible biopsy needle and said cannula through said guide assembly to a desired orientation and position for biopsying the tissue of the patient,
wherein said flexible biopsy needle and said cannula are insertable together through said guide channel with said bending section of said needle inside said bendable portion of said elongate body of said cannula, said guide channel physically bends said flexible biopsy needle and said cannula to a bent configuration when said flexible biopsy needle and said cannula are advanced therethrough, and in said bent configuration, said needle and said cannula extend through an angle of at least forty degrees.

17. The needle biopsy system according to claim 16, further comprising:

an ultrasonic probe capable of being inserted into the patient and adapted to scan the tissue to be biopsied, said guide assembly coupled to said probe.

18. The needle biopsy system according to claim 16, further comprising:
a biopsy gun coupled to said needle and said cannula and configured to fire said needle and said cannula when said needle and said cannula are disposed in said bent configuration.

19. The needle biopsy system according to claim 18, wherein:
said biopsy gun is a disposable biopsy gun.

20. The needle biopsy system according to claim 16, wherein:
said tissue piercing distal end, said sampling section, said bending section, and said body portion of said needle are made from nitinol.

21. The needle biopsy system according to claim 16, wherein:
said guide assembly includes at least one guide tube which defines said at least one guide channel, and said at least one guide tube is metal.

22. The needle biopsy system according to claim 21, wherein:
each guide tube includes a straight section and a curved portion, said curved portion for physically bending said biopsy needle and extending through an angle of at least forty five degrees.

23. The needle biopsy system according to claim 22, wherein:
said curved portion extends through an angle of at least sixty degrees.

24. The needle biopsy system according to claim 23, wherein:
said curved portion extends through an angle of at least seventy degrees.

25. The needle biopsy system according to claim 16, wherein:
said second circular cross section of said body portion of said needle has a diameter of less than 0.04 inches.

26. The needle biopsy system according to claim 25, wherein:
said first circular cross section of said bending section of said needle has a diameter of less than 0.03 inches.

27. The needle biopsy system according to claim 16, wherein:
said needle and said cannula are rotatable about a central axis extending through said guide channel, and said first circular cross section of said bending section of said needle provides for reduced friction during deployment of either said needle from said cannula or said cannula from said needle in any arbitrary rotational orientation of said needle and said cannula about said central axis of said guide channel.

28. The needle biopsy system according to claim 27, wherein:
in said bent configuration, said tissue piercing distal ends of said needle and said cannula are disposed adjacent each other, said bending section of said needle is disposed within said bendable portion of said cannula, and said needle is distally advanceable relative to said cannula from said bent configuration by application of a force to said needle, said force no more than 15 ounces.

29. The needle biopsy system according to claim 28, wherein:
said force is no more than 10 ounces.

\* \* \* \* \*

UNITED STATES PATENT AND TRADEMARK OFFICE
CERTIFICATE OF CORRECTION

PATENT NO. : 9,044,216 B2  
APPLICATION NO. : 12/834357  
DATED : June 2, 2015  
INVENTOR(S) : Michael O'Laughlin Page 1 of 1

It is certified that error appears in the above-identified patent and that said Letters Patent is hereby corrected as shown below:

In the Specification

1. Column 8, line 4, 'cannula 12' should read --the cannula 12--; column 8, line 38, '72°-17°-10°45°' should read --72° - 17° - 10° = 45°--.

2. Column 9, lines 47-48, 'guide assembly 11' should read --the guide assembly 11--; column 9, line 64, 'cannula 12' should read --the cannula 12--.

3. Column 10, line 6, 'cannula 12' should read --the cannula 12--; column 10, line 33, 'needle's 10's bending section 20' should read --needle 10's bending section 20--.

In the Claims

4. Column 14, line 9, of claim 16, 'a cannula having proximal end' should read --a cannula having a proximal end--.

5. Column 16, line 5, of claim 25, 'cross section' should read --cross-section--.

6. Column 16, line 9, of claim 26, 'cross section' should read --cross-section--.

7. Column 16, line 15, of claim 27, 'cross section' should read --cross-section--.

Signed and Sealed this  
Sixth Day of October, 2015

Michelle K. Lee  
*Director of the United States Patent and Trademark Office*